United States Patent [19]

Patterson et al.

[11] Patent Number: 5,314,690
[45] Date of Patent: May 24, 1994

[54] METHOD AND COMPOSITION FOR TREATING IGE-MEDIATED ALLERGIES

[75] Inventors: Roy Patterson, Wilmette; Kathleen E. Harris, Glenview, both of Ill.

[73] Assignee: Northwestern University, Evanston, Ill.

[21] Appl. No.: 934,553

[22] Filed: Aug. 21, 1992

Related U.S. Application Data

[63] Continuation-in-part of Ser. No. 705,071, May 24, 1991, abandoned.

[51] Int. Cl.$^5$ .................... A61K 37/24; A61K 39/35; A61K 39/36
[52] U.S. Cl. ........................ 424/88; 424/91; 424/114; 514/15; 514/885
[58] Field of Search .................. 514/15; 424/88-92

[56] References Cited

U.S. PATENT DOCUMENTS 4,740,371 4/1988 St. Remy et al. ............ 424/85
4,946,945 8/1990 Wojdani ..................... 530/402

OTHER PUBLICATIONS

Anderson, et al. "Preseasonal Polymerized Ragweed Immunotherapy in Canine Allergic Inhalant Dermatitis (AID)-A Pilot Study," J. Allergy Clin. Immunol. 69:116, (1982) (Part 2).
Bienenstock, et al. "Neuroendocrine Regulation of Mucosal Immunity" Immunol. Invest. 18:69-76 (1989).
Chang, et al. "Amino-acid Sequence of Substance P" Nature New Biology 232:86-87 (1971).
Cook, et al. "Serological Evidence of Immunity With Coexisting Sensitization in a Type of Human Allergy (Hay Fever)" J. Experimental Medicine 62:744-750 (1935).
Euler, et al. "An Unidentified Depressor Substance in Certain Tissue Extracts" J. Physiology 72:74-87 (1931).
Fuller, et al. "Effect of Substance P on Cardiovascular and Respiratory Function in Subjects" American Physio. Soc. pp. 1473-1479 (1987).
Ghory, et al. "In vitro IgE Formation by Peripheral Blood Lymphocytes From Normal Individuals and Patients With Allergic Bronchopulmonary Aspergillosis" Clin. Exp. Immunol. 40:581-585 (1980).
Goetzl, et al. "Neuropeptides, Mast Cells and Allergy: Novel Mechanisms and Therapeutic Possibilities" Clin. Experimental Allergy 20, Supplement 4:3-7 (1990).
Machiels, et al. "Allergic Bronchial Asthma Due to *Dermatophagoides pteronyssinus* Hypersensitivity Can Be Efficiently Treated by Inoculation of Allergen-Antibody Complexes" J. Clin. Invest. 85:1024-1035 (1990).
Macy, et al. "Enhanced ELISA: How to Measure Less Than 10 Picograms of a Specific Protein (Immunoglobulin) in Less Than 8 Hours" FASEB J. 2:3003-3009 (1988).
Melam, et al. "Correlations Between Clinical Symptoms, Leukocyte Sensitivity, Antigen-Binding Capacity, and Prausnitz-Kustner Activity in a Longitudinal Study of Ragweed Pollinosis" J. Allerg. 46:292-299 (1970).
McGillis, et al. "Substance P and Immunoregulation" Fed. Proceed. 46:196-199 (1987).
O'Dorisio, et al. "Vasoactive Intestinal Piptide and Neuropeptide Modulation of the Immune Response" J. Immunol. 135:792-796 (1985).
Patterson, et al. I "Aerosolized Antigen Dose-response Studies in Asthmatic Monkeys" J. Lab. Clin. Med. 92:283-289 (1978).
Patterson, et al. II "Animal Models of the Asthmatic State" Annual Rev. of Med. 25:53-68 (1974).

(List continued on next page.)

*Primary Examiner*—Robert J. Hill, Jr.
*Assistant Examiner*—David L. Fitzgerald
*Attorney, Agent, or Firm*—Tilton, Fallon, Lungmus & Chestnut

[57] ABSTRACT

The present invention relates to a method and preparations for reducing IgE antibodies to allergens in allergic subjects wherein substance P and an allergen or fragments of allergens or haptens acting as allergens are administered together to the allergic subjects. The method can be used to treat humans and animals including dogs, cats, horses and subhuman primates.

10 Claims, 11 Drawing Sheets

OTHER PUBLICATIONS

Patterson, et al. III "Effects of Combined Receptor Antagonists of Leukotriene $D_4$ ($LTD_4$) and Platelet-Activating Factor (PAF) on Rhesus Airway Responses to $LTD_4$, PAF and Antigen" Int. Arch. Allergy Appl. Immunol. 88:462–470 (1989).

Patterson, et al. IV "Induction of IgE-mediated Cutaneous, Cellular, and Airway Reactivity in Rhesus Monkeys by *Ascaris suum* Infection" J. Lab. Clin. Med. 101:864–872 (1983).

Patterson, et al. V "*In Vitro* Production of IgE by Human Peripheral Blood Lymphocytes: Effect of Cholera Toxin and $\beta$ Adrenergic Stimulation" J. Immunol. 117:97–101 (1976).

Patterson, et al. VI "*In vitro* production of IgE by Lymphocytes From a Patient With Hyperimmunoglobulinaemia E, Eosinophilia and Increased Lymphocytes Carrying Surface IgE" Clin. Exp. Immunol. 20:265–272 (1975).

Patterson, et al. VII "Living Histamine–Containing Cells From the Bronchial Lumens of Humans" J. Clin. Invest. 59:217–225 (1977).

Patterson, et al. VIII "Parallel Induction of IgE-mediated Ascaris Antigen Airway Responses and Increased Carbachol Airway Reactivity in Rhesus Monkeys by Infection With Ascaris suum" J. Clin. Lab. Med. 106:293–297 (1985).

Patterson, et al. IX "Reagin-mediated Asthma in Rhesus Monkeys and Relation to Bronchial Cell Histamine Release and Airway Reactivity to Carbocholine" J. Clin. Invest. 57:586–593 (1976).

Patterson, et al. X "Respiratory Responses in Subhuman Primates With Immediate Type Hypersensitivity" J. Lab. Clin. Med. 73:924–933 (1969).

Patterson, et al. XI "Rhesus Monkey Responses to Substance P" Int. Arch. Allergy Immunol. 91:374–379 (1990).

Patterson, et al. XII "Studies of Platelet Activating Factor in Primates" New Horizons in Platelet Activating Factor Research, pp. 311–316 (1987).

Payan, et al. "Binding Characteristics and Affinity Labeling of Protein Constituents of the Human IM-9 Lymphoblast Receptor for Substance P" J. Biol. Chem. 261:14321–14329 (1986).

Payan, et al. "Substance P Recognition by a Subset of Human T Lymphocytes" Amer. Soc. Clin. Invest., Inc. 74:1532–1539 (1984).

Siemion, et al. "Immunoregulatory Activity of Substance P Fragments" Molecular Immunol. 27:887–890 (1990).

Stanworth, et al. "Allergy Treatment With a Peptide Vaccine" Lancet 336:1279–1281 (1990).

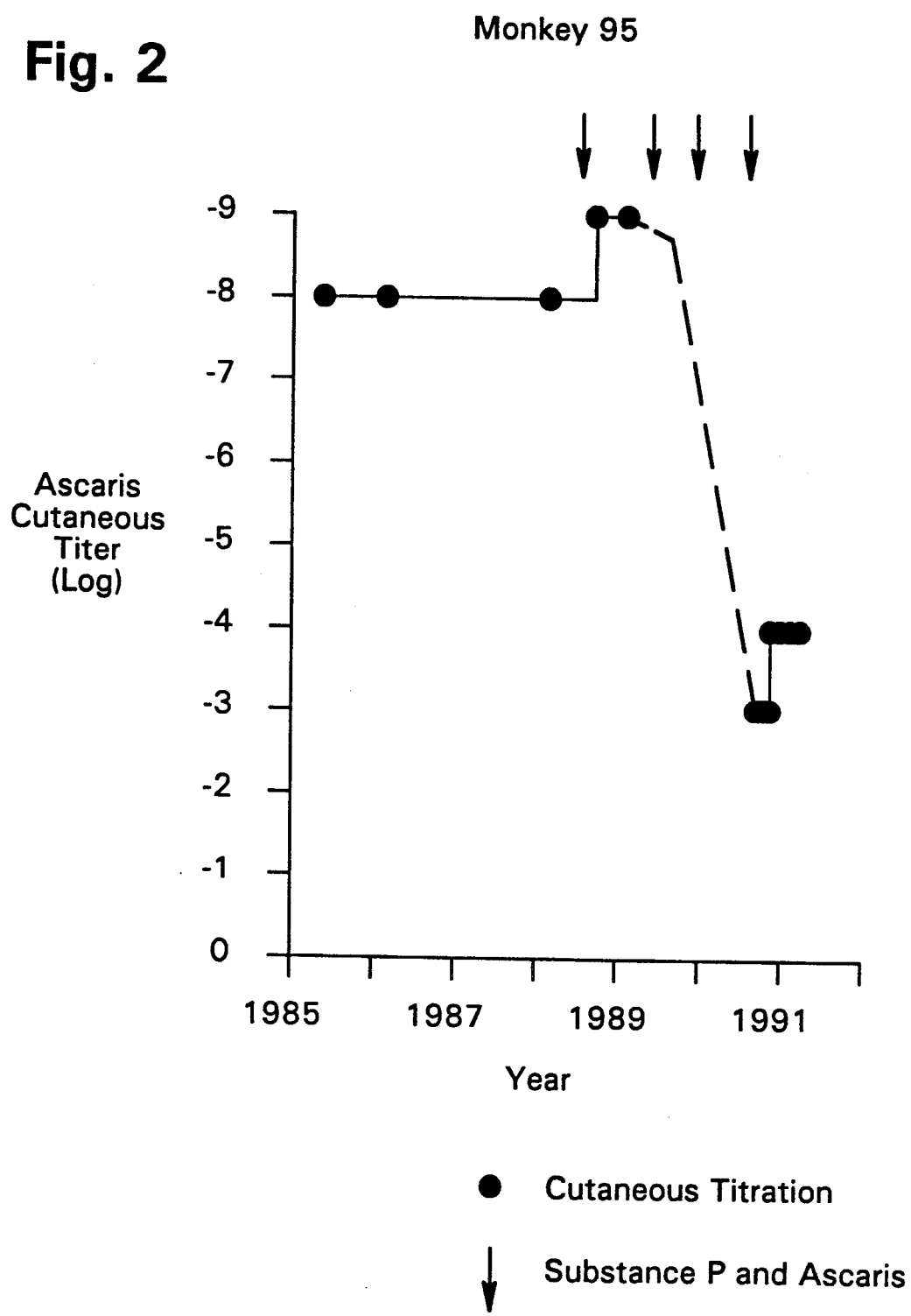

Fig. 2

Monkey 95

Ascaris Cutaneous Titer (Log)

Year

● Cutaneous Titration

↓ Substance P and Ascaris

METHOD AND COMPOSITION FOR TREATING IGE-MEDIATED ALLERGIES

GRANT REFERENCES

Research leading to the invention was supported in part by USPHS GRANT NIAID AI 20060 and NIAID Asthma and Allergic Diseases Center Grant AI 11403. The U.S. Government has rights therein.

RELATED APPLICATION

This application is a continuation-in-part of co-pending application Ser. No. 705,071, filed May 24, 1991, now abandoned.

FIELD OF THE INVENTION

This invention relates to a method for reducing IgE antibodies to specific allergens, and to pharmaceutical compositions useful therefor. More particularly, this invention relates to a method of treating allergy, involving administering substance P together with a specific allergen.

DESCRIPTION OF RELATED ART

Immediate hypersensitivity (or anaphylactic response) is a form of allergic reaction which develops very quickly, i.e. within seconds or minutes of exposure of the patient to the causative allergen, and it is mediated by IgE antibodies made by B lymphocytes. In nonallergic patients, there is no IgE antibody of clinical relevance; but, in a person suffering with allergic diseases, IgE antibody mediates immediate hypersensitivity by sensitizing mast cells which are abundant in the skin, lymphoid organs, in the membranes of the eye, nose and mouth, and in the respiratory tree and intestines.

Mast cells have surface receptors for IgE, and the IgE antibodies in allergy-suffering patients become bound to them. When the bound IgE is subsequently contacted by the appropriate allergen, the mast cell is caused to degranulate and to release various substances called bioactive mediators, such as histamine, into the surrounding tissue. It is the biologic activity of these substances which is responsible for the clinical symptoms typical of immediate hypersensitivity; namely, contraction of smooth muscle in the airways or the intestine, the dilation of small blood vessels and the increase in their permeability to water and plasma proteins, the secretion of thick sticky mucus, and in the skin, redness, swelling and the stimulation of nerve endings that results in itching or pain.

IgE antibody results in allergic rhinitis, allergic asthma (such as cat asthma); and IgE is an important factor in many cases of mixed allergic and nonallergic asthma of which house dust mite is an international example. These chronic allergic diseases are significant in 10 to 20 percent of the population, world-wide. IgE antibody can mediate reactions which are potentially fatal—anaphylaxis.

The IgE antibody can persist for years even in the absence of exposure to causative allergen. The IgE (allergic) antibody production cannot be terminated by any previously known therapeutic manipulation. IgE antibody cannot be removed from the body, except for neutralization of the antibody by desensitization (as for penicillin or insulin allergy). This requires continuous administration of antigen to bind IgE antibody. Although allergic antibody production may decline spontaneously, this is not common; when it does occur, a span of several years is usually required. Thus, both allergic antibodies and clinical allergic reactions usually persist at least for years or for decades in man.

A few treatment schemes have been devised to reduce or eliminate an allergic response. Allergen injection therapy (allergen immunotherapy) is known to reduce the severity of allergic rhinitis. This treatment is theorized to involve the production of a different form of antibody, a protective antibody which is termed a "blocking antibody". Cooke, RA et al., Serologic Evidence of Immunity with Coexisting Sensitization in a Type of Human Allergy, Exp. Med. 62:733 (1935).

Other attempts to treat allergy involving modifying the allergen have been proposed, that is, attempts have been made to modify the allergen chemically so that its ability to cause an immune response in the patient is unchanged, while its ability to cause an allergic reaction is substantially altered.

St. Remy et al., U.S. Pat. No. 4,740,371, discloses a complex for treating allergies involving a combination of the specific allergen that causes the allergic reaction and the corresponding specific antibody. The injection of the complex into a patient is said to reduce a patient's allergic reaction to that specific allergen.

Others have suggested that certain human proteins can neutralize IgE by blocking it from interacting with the mast cells, but this has not been established clearly as a clinically effective therapy. Stanworth, Dr. et al., Allergy Treatment with a Peptide Vaccine, Lancet 336:1279-81 (1990).

Recently, certain neuropeptides have been shown to have immunomodulating properties. For example, functional studies have shown that substance P can influence lymphocyte function by specific receptor mediated mechanisms. Further, substance P has been shown to modulate distinct immediate hypersensitivity responses by stimulating the generation of arachidonic acid-derived mediators from mucosal mast cells. J. McGillies, et al., Substance P and Immunoregulation, Fed. Proc. 46:196-9 (1987).

Substance P is a neuropeptide first identified in 1931 by Von Euler and Gaddum. An unidentified depressor substance in certain tissue extracts, J. Physiol. (London) 72:74-87 (1931). Its amino acid sequence, Arg-Pro-Lys-Pro-Gln-Gln-Phe-Phe-Gly-Leu-Met-NH$_2$ (Sequence Id. No. 1) was reported by Chang et al. in 1971. Amino acid sequence of substance P, Nature (London) New Biol. 232:86-87 (1971).

The immunoregulatory activity of fragments of substance P has been studied by Siemion, et al. Immunoregulatory Activity of Substance P Fragments, Molec. Immunol. 27:887-890 (1990). They reported that the C-terminal SP$^{7-11}$ pentapeptide (Phe-Phe-Gly-Leu-Met-NH$_2$) (Sequence Id. No. 2) suppressed the immune response in vitro, and they also observed a distinct immuno-suppression in vivo. In contrast, the N-terminal SP$^{1-4}$ (Gly-Pro-Arg-Pro) (Sequence Id. No. 5) tetrapeptide only moderately suppressed the immune response at low doses, while at higher doses the immune response was slightly stimulated. None of these studies dealt with IgE or IgE antibody.

SUMMARY OF INVENTION

This invention is based on the surprising discovery that substance P administered together with a specific allergen (or allergens) can drastically reduce the amount of IgE antibodies to the allergen. A new method of allergy therapy has thereby resulted. The invention also provides new pharmaceutical compositions which can comprise a mixture of substance P with a specific allergen (or allergens), for example, in a suitable form such as by injectable administration. This invention also contemplates administering fragments of substance P with a specific allergen or allergens.

IgE antibody is the antibody which results in human allergic diseases such as hay fever and allergic asthma and analogous conditions in animals. The levels of IgE antibody in an allergic individual, man or animal, can be quantitated by end point cutaneous titration. These IgE levels persist for years with little variation. There is no previously known treatment which has been found to significantly alter these IgE antibody levels in man or animals with the exception of very intense allergen immunotherapy [Melam H, Pruzansky JJ, Patterson R: Correlations between Clinical Symptoms, Leukocyte Sensitivity, Antigen-Binding Capacity and P-K Activity in a Longitudinal Study of Ragweed Pollinosis. J. Allergy. 46:292-9 (1970)] and in allergen desensitization as for penicillin, a highly dangerous procedure. The animal experiments which lead to the present invention were therefore not designed to produce this result. We were studying the bronchospastic effects of substance P and other substances on allergic monkeys.

A research colony of rhesus monkeys is maintained at the Northwestern University Medical School, Chicago, Illinois, USA. Some of these animals are allergic to Ascaris antigen with allergic asthma and have marked skin reactivity to Ascaris antigen of long duration (analogous to the allergic human population). Experiments were designed to evaluate airway effects of the aerosolized substance P, a neurokinin, and allergen in rhesus monkeys. Remarkably, the level of IgE antibody declined in seven of seven monkeys, and dramatically in six of the seven monkeys.

The foregoing experimental discovery was interpreted by the inventors of this application as showing that substance P plus allergen, appropriately delivered to a subject (man or animal), is capable of sharply reducing IgE allergic antibody, thereby resulting in improved control and possibly complete cures of allergic diseases. Such reduction of IgE antibodies in allergic patients has been a long sought goal which has eluded allergy researchers for many years. Finding a therapy which can accomplish this result was therefore highly unexpected.

The Ascaris-allergic rhesus monkeys in the Northwestern University research colony used as test subjects had a dramatic decrease in their Ascaris allergy. This limited the further use of these monkeys for the research purposes for which the colony had been developed--a loss of research effectiveness of the colony but with a great dividend to scientific knowledge concerning IgE reduction in allergic subjects.

BRIEF DESCRIPTION OF THE FIGURES

FIG. 2 shows Ascaris endpoint cutaneous titers of monkey 95;

DESCRIPTION OF THE INVENTION

Figure 3:
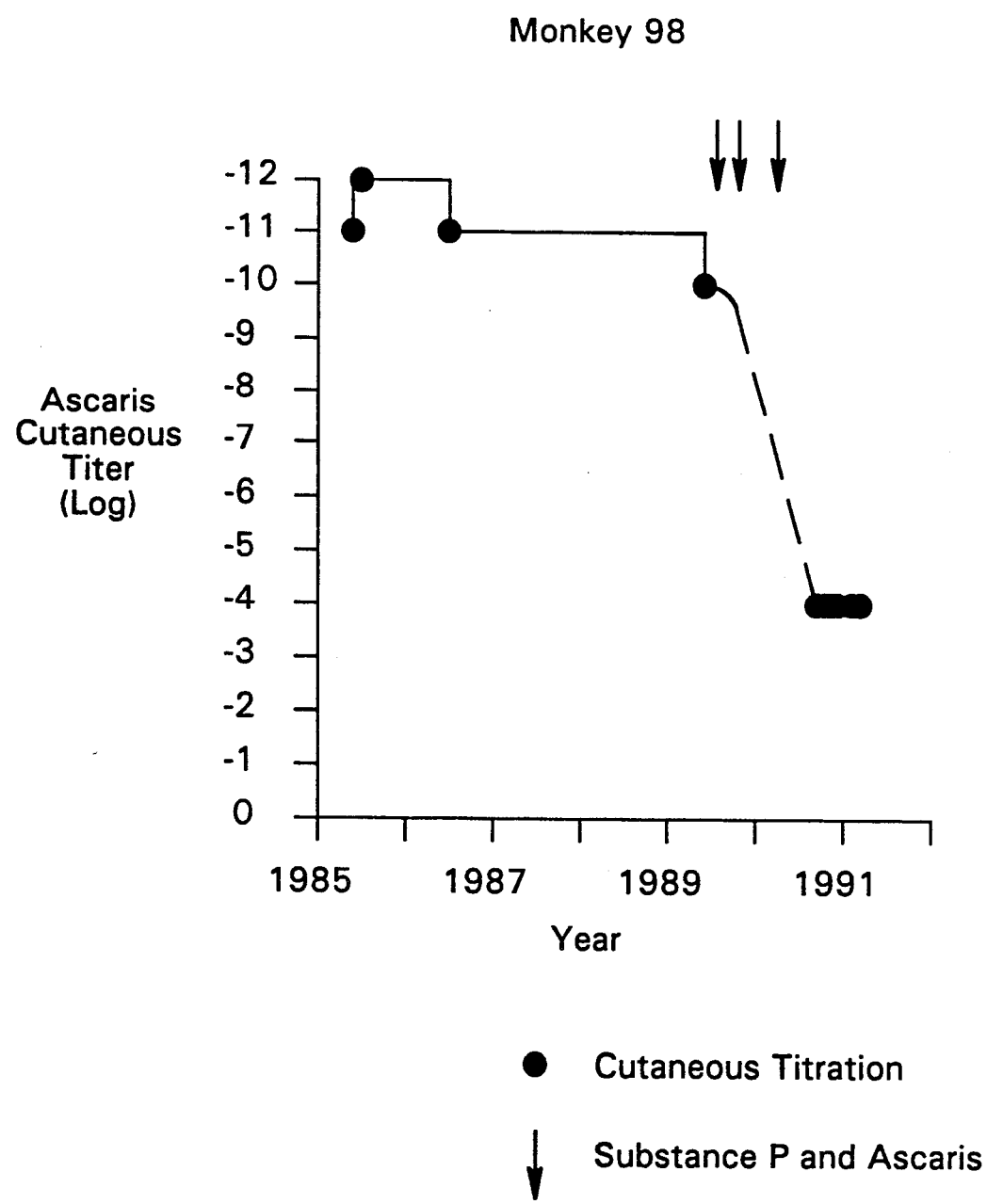
FIG. 3 shows Ascaris endpoint cutaneous titers of monkey 98.

We have found that substance P administered together with an allergen can reduce the amount of IgE produced to that allergen. This method offers highly significant advantages over prior art methods for treating allergy. Importantly, no human biological material, such as antibodies, needs to be introduced into the patient. This eliminates health risk associated with biological material.

RESEARCH LEADING TO INVENTION

During our long term research on allergic monkeys we evaluated the effect of aerosolized substance P and an allergen (*Ascaris suum* antigen) on monkeys. Previous studies using the rhesus monkey model of IgE mediated asthma had shown that the animals have individual characteristics analogous to the individuality of human asthmatics. Patterson, R, et al., Respiratory Responses in Subhuman Primates With Immediate Type Hypersensitivity, J. Lab. Clin. Med. 73:924-33 (1969) . Patterson R, Harris KE, Pruzansky JJ: Induction of IgE-mediated Cutaneous, Cellular, and Airway Reactivity in Rhesus Monkeys by *Ascaris suum* Infection. J. Lab. Clin. Med. 101:864-72 (1983).

All animals studied had cutaneous reactivity to Ascaris antigen. Subsequent to our studies on the use of receptor antagonists in the modification of primate allergic asthma, we were involved with a study of the relation of neurokinins and asthma, using the monkey IgE mediated Ascaris airway response. In a series of studies, we had observed that substance P given just prior to Ascaris allergen challenge increased the airway response to Ascaris. This increase was transient, disappearing spontaneously within 12 months. On the completion of these experiments, selected monkeys were skin tested as a routine procedure and it was unexpectedly discovered that skin reactivity to Ascaris had decreased. Consequently, all seven monkeys, which had received aerosolized substance P and Ascaris antigen, were skin tested and surprisingly found to have decreased skin reactivity. The IgE antibody to Ascaris was greatly reduced, and in one animal virtually eliminated.

SCOPE OF INVENTION

In the context of this invention, the term allergen means a specific type of antigen which can trigger an allergic response which is mediated by IgE antibody. The method and preparations of this invention extend to a broad class of such allergens and fragments of allergens or haptens acting as allergens. These can include all the specific allergens that can cause an IgE mediated response in allergic subjects. This invention is therefore believed to be useful for the treatment of allergic diseases in humans, other primates, and mammalian subjects, such as dogs, cats, and horses. The scope of the invention therefore encompasses the following allergic diseases.

| Species | |
|---|---|
| | Allergic Diseases Due to IgE |
| HUMAN | Allergic rhinitis (hay fever) |
| | Allergic Asthma |
| | Atopic dermatitis |
| | Anaphylaxis |
| | Food Allergy |
| | Drug Allergy |
| | Urticaria (hives) |
| | Angioedema |
| | Allergic conjunctivitis |
| | Allergens related to IgE Mediated Diseases |
| | Environmental Aeroallergens |
| | Weed pollen allergens |
| | Grass pollen allergens |
| | Tree pollen allergens |
| | House dust mite allergens |
| | Storage mite allergens |
| | Mold spore allergens |
| | Animal allergens (examples by species - cat, dog, guinea pig, hamster, gerbil, rat, mouse) |
| | Animal allergens (examples by source - epithelial, salivary, urinary proteins) |
| | Food Allergens |
| | All foods containing proteins. Common examples: Crustaceans; nuts, such as peanuts; citrus fruits |
| | Insect Allergens (Other than mites listed above) |
| | Venoms: Hymenoptera, yellow jacket, honey bee, wasp, hornet, fire ant. |
| | Other environmental insect allergens from cockroaches, fleas, mosquitoes, etc. |
| | Bacteria such as streptococcal antigens |
| | Parasites such as Ascaris antigen |
| | Viral Antigens |
| | Drug Allergens |
| | Antibiotics |
| | penicillins and related compounds; other antibiotics |
| | Whole Proteins such as hormones (insulin), enzymes (Streptokinase), all drugs and their metabolites capable of acting as incomplete antigens or haptens. |
| | Industrial Chemicals and metabolites capable of acting as haptens and stimulating the immune system. Examples are the acid anhydrides (such as trimellitic anhydride) and the isocyanates (such as toluene diisocyanate) |
| | Occupational Allergens such as flour in Baker's asthma, castor bean, coffee bean, and industrial chemicals described above. |
| | Examples of IgE Mediated Diseases |
| DOG | Seasonal dermatitis |
| | Perennial dermatitis |
| | Rhinitis |
| | Conjunctivitis |
| | Allergic Asthma |
| | Drug Reactions |
| | Examples of Allergens Important for Dogs |
| | All environmental allergens important in humans (except for dog allergens). Parasitic allergens and flea allergens are of particular importance. Human proteins are an addition for dogs. |
| CAT | Diseases: |
| | Dermatitis and respiratory. |

| Species | |
|---|---|
| | All allergens important in dogs and humans except cat. Food allergens are of particular importance. |
| HORSES | Diseases: |
| | Respiratory such as "heaves". |
| | Dermatitis. Examples of Allergens: mold spores, house dust mites, storage mites. |
| PRIMATES OTHER THAN HUMAN. EXAMPLE: | Diseases: |
| | Allergic asthma, allergic dermatitis |
| | Examples: Pollen allergens, mold |
| Rhesus Monkey | allergens, mite allergens, parasitic allergens. |

THE SUBSTANCE P REAGENT

Substance P is a neuropeptide having the amino acid sequence Arg-Pro-Lys-Pro-Gln-Gln-Phe-Phe-Gly-Leu-Met-NH$_2$ (Sequence Id. No. 1). The complete sequence is presently preferred, but it is postulated that fragments thereof can also be used for reduction of IgE antibody in all mammals. The fragments should be selected to have the IgE reducing activity of substance P. For example, since substance P is enzymatically degraded in the body, it is expected that fragments of substance P will also function with an allergen to reduce IgE antibodies to allergen in allergic subjects. Examples of degradation products include:

I. pGlu-Phe-Phe-Gly-Leu-Met-NH2 (Sequence Id. No. 3)
II. Phe-Phe-Gly-Leu-Met-NH2 (Sequence Id. No. 2)
III. Arg-Pro-Lys-Pro (Sequence Id. No. 4)
IV. Gly-Pro-Arg-Pro (Sequence Id. No. 5)

See Siemion et al., Immunoregulatory Activity of Substance P Fragments, Molec. Immunol. 27:887–90 (1990).

Peptides I–IV were studied by Siemion to assess their immunoregulatory activity Id.

Siemion studied the immunoregulatory activity of substance P fragments noting that the C-terminal pentapeptide was an immunosuppressant in vivo and in vitro. The N-terminal tetrapeptide was suppressive at one dose and stimulatory at a higher dose. The results suggested the the N-terminal portion of substance P is connected with the immunostimulatory activity of the peptide and the C-terminal portion possesses the immunosuppressive properties.

The studies of the immunoregulatory activity of substance P fragments by Siemion did not address the activity of these fragments on the cellular production of IgE and IgE antibody. The activity of these fragments on IgE production can be tested by studying their effect on in vitro production of IgE by human peripheral blood cells. These techniques have been established in our Northwestern University Allergy-Immunology laboratory [Patterson R, Suszko IM, Hsu CS, Roberts M, Oh SH: In Vitro Production of IgE by Lymphocytes From a Patient With Hyperimmunoglobulinemia E. Eosinophilia and Increased Lymphocytes Carrying Surface IgE. Clin. Exp. Immunol. 20:265–72 (1970); Patterson R, Suszko IM, Metzger WJ, Roberts M: In Vitro Production of IgE by Human Peripheral Blood Lymphocytes: Effect of Cholera Toxin and Beta Adrenergic Stimulation. J. Immunol. 117:97–101 (1976). Ghory AC, Patterson R, Roberts M, Suszko IM: In Vitro IgE Formation by Peripheral Blood Lymphocytes From Normal Individuals and Patients With Allergic Bronchopulmonary Aspergillosis. Clin. Exp. Immunol. 40:581-5 (1980)]. The techniques can be enhanced by the addition of interleukin-4 and measured by an amplified IgE immunoassay. Macy E, Kemeny M, Saxon A: Enhanced ELISA: How to Measure Less Than 10 Picograms of a Specific Protein (Immunoglobulin in Less than 8 hours, FASEB J. 2:3003-9 (1988).

Substance P and the specific allergen or specific allergens are administered so that they act together, for example, they can be administered together or substantially concurrently. Such administration may use any route which results in systemic absorption such as the following procedure and routes: substantially simultaneously, or in sequence, such as separately within one hour, substance P being administered first, or in a reverse sequence. The specific allergen should be administered prior to the complete enzymatic breakdown of substance P and its fragments. Substance P and the allergen can be administered by several known routes, which include: by aerosol to the bronchial tree of the lungs; to the nose by spray or nose drops; sublingually; orally; and by injection, including subcutaneously, intramuscularly, or intravenously, as for example, in emergency situations involving reactions to penicillins or insulin, and buccal administration. Transdermal routes are believed to be especially desirable of administration of fragments of substance P.

Substance P and the specific allergen can be delivered simultaneously or in close time sequence by different routes, e.g. substance P sublingually and the specific allergen subcutaneously, or in other combinations. Substance P or equivalent can be administered by any route listed above in doses ranging from 0.01 mg to 10 mg as single or divided doses. Parts of the total dose may be administered by different routes listed under routes of administration. Whatever the procedure and administration routes used, it will usually be desirable to administer repeated doses of the allergen and substance P at suitable intervals. The treatment may possibly be continued until the IgE antibodies to the allergen are appreciably reduced, and preferably until the IgE antibodies are substantially completely eliminated.

Common allergens (as currently used in allergen injection therapy) are given in the following exemplary dosages: Allergens are expressed as weight of allergen per volume of original extracting solution (w/v). For example, preparation of short ragweed (*Ambrosia artemisiifolia* (*elatior*)) extract is prepared from 1 g of ragweed pollen in 10 ml of solution giving a 1:10 w/v extract of ragweed. Doses of ragweed with substance P could range from 0.1 ml of 1:10,000 to 1 ml of 1:10 in the individual case. Similar weight per volume dosages would apply to all environmental pollens, mold spores, mites and animal dander extracts. More than one allergen may be given with substance P. For example, a patient allergic to ragweed, grass and tree pollens could receive substance P plus ragweed, grass and tree pollen extracts at the same exposure. Specifically, in terms of administration to a patient with ragweed or pollen allergy, substance P is inhaled using a bronchial inhalation and then ten minutes after inhalation of substance P, increasing doses of ragweed or grass pollen allergen can be delivered by inhalation. A metered dose machine could be used to administer both. Once per week for a period of four weeks, increasing doses of substance P are inhaled followed immediately by allergen. Quantitative skin tests are performed to the pollen allergen to determine the change in reactivity to the allergen over the next several months.

Additionally, it is expected that treatment of allergies to venoms can use the method of this invention. For example, the treatment of a venom allergy can involve graded doses of substance P plus graded doses of honey bee venom ranging from 0.01 micrograms of venom to 100 micrograms of venom. Multiple venoms could be simultaneously administered.

Still another example of treatment according to the present method involves administration of substance P in doses described above plus a drug such as penicillin in doses ranging from 0.001 mg to 250 mg.

EXAMPLE 1

A monkey with IgE mediated asthma has certain characteristics. The established characteristics of rhesus monkeys with IgE mediated reactivity to Ascaris antigen include: 1) Cutaneous reactivity to Ascaris antigen which is always present in an animal with airway reactivity to Ascaris antigen. Patterson R, Talbot CH: Respiratory Responses in Subhuman Primates with Immediate Type Hypersensitivity J. Lab. Clin. Med. 73:924-33 (1969); Patterson R, Harris KE: Parallel Induction of IgE-Mediated Ascaris Antigen Airway Responses and Increased Carbachol Airway Reactivity in Rhesus Monkeys by Infection With *Ascaris suum*. J. Lab. Clin. Med. 106:293-7 (1985); 2) An animal may have cutaneous reactivity with no airway reactivity. Patterson R, Talbot CH: Respiratory Responses in Subhuman Primates with Immediate Type Hypersensitivity. J. Lab. Clin. Med. 73:924-33 (1969); Patterson R, Harris KE: Parallel Induction of IgE-mediated Ascaris Antigen Airway Responses and Increased Carbachol Airway Reactivity in Rhesus Monkeys by Infection with *Ascaris suum*. J. Lab. Clin. Med. 106:293-7 (1985); Patterson R, Harris KE, Suszko IM, Roberts M.: Reagin-mediated Asthma in Rhesus Monkeys and Relation to Bronchial Cell Histamine Release and Airway Reactivity to Carbocholine. J. Clin. Invest. 57:586-93 (1976), Patterson R, Kelly JF: Animal Models of the Asthmatic State. Annu. Rev. Med. 24:53-68 (1974); 3) An animal with airway reactivity to Ascaris may be consistently positive for years. Patterson R, Harris KE, Suszko IM, Roberts M: Reagin-mediated Asthma in Rhesus Monkeys and Relation to Bronchial Cell Histamine Release and Airway Reactivity to Carbocholine. J. Clin. Invest. 57:586-93 (1976); Patterson R, Kelly JF: Animal Models of the Asthmatic State. Annu. Rev. Med. 25:53-68 (1974); 4) An animal with a negative response to airway challenge with Ascaris cannot be made responsive by repeated airway challenge with Ascaris antigen. Patterson R, Kelly JF: Animal Models of the Asthmatic State. Annu. Rev. Med. 25:53-68 (1974); Patterson R, Harris KE, Pruzansky JJ: Induction of IgE Mediated Cutaneous, Cellular, and Airway Reactivity in Rhesus Monkeys by *Ascaris suum* Infection. J. Lab. Clin. Med. 101:864-72 (1983); 5) An animal that previously had an airway response to Ascaris antigen may be consistently negative to airway challenge with Ascaris antigen and this negativity will persist in spite of repeated airway challenge with Ascaris antigen and 6) The only manner in which airway or persistent cutaneous responsiveness to Ascaris antigen occurs is a residual of natural parasitic infection in youth or active infection as an adult with *Ascaris suum* ova. Patterson R, Talbot, CH: Respiratory Responses in Subhuman Primates with Immediate Type Hypersensitivity. J. Lab. Clin. Med. 73:924-33

(1969). Patterson R, Harris KE: Parallel Induction of IgE-mediated Ascaris Antigen Airway Responses and Increased Carbachol Airway Reactivity in Rhesus Monkeys by Infection with *Ascaris suum*. J. Lab. Clin. Med. 106:293-7 (1985); Patterson R, Harris KE, Suszko IM, Roberts M: Reagin-mediated Asthma in Rhesus Monkeys and Relation to Bronchial Cell Histamine Release and Airway Reactivity to Carbocholine. J. Clin. Invest. 57:586-93 (1976); Patterson R, Kelly JF: Animal Models of the Asthmatic State. Annu. Rev. Med. 25:53-68 (1974); Patterson R, Harris KE, Pruzansky JJ: Induction of IgE-mediated Cutaneous, Cellular, and Airway Reactivity in Rhesus Monkeys by *Ascaris suum* Infection. J. Lab. Clin. Med. 101:864-72 (1983); A colony of rhesus monkeys having these characteristics is maintained by Northwestern University Medical School. Allergic monkeys used in this example are from this colony.

Animals

Healthy adult male and female rhesus monkeys (*Macaca mulatta*) weighing 6 to 17 kg were used. Three types of monkeys were studied, those previously characterized as being consistent respiratory responders to Ascaris, those that had previously been airway sensitive to Ascaris antigen but were no longer airway reactive but retained skin reactivity to Ascaris antigen and animals that never have had airway reactivity but have had cutaneous reactivity to Ascaris antigen.

Antigen and Pharmacologic Agents

*Ascaris suum* antigen used in these studies was purchased from Greer Laboratories (Lenoir, NC). Substance P was purchased from Sigma Chemical Co. (St. Louis, MO).

Cutaneous Reactivity

Monkeys were anesthetized and received 5 ml of 0.5% Evans' blue dye intravenously. Serial 10-fold dilutions of Ascaris were made in buffered saline and were injected intracutaneously. A positive response was one that produced a deep blue area at least 10 mm in diameter. The endpoint cutaneous titer was considered to be the last 10-fold dilution that elicited blueing.

Determination of Pulmonary Function Parameters

Animals were anesthetized with sodium pentobarbital before all studies and baseline pulmonary function measurements. The following measurements were obtained: breathing frequency (f), pulmonary resistance ($R_L$), peak expiratory flow rate (PEFR), tidal volume ($V_T$), and dynamic compliance (Cdyn). The peak expiratory flow rate is the maximal expiratory flow during quiet (nonforced) expiration. Results were expressed as percent change from baseline. A positive response was defined as a response showing abnormalities in four of the five parameters greater than the following: f+20%, $R_L$+25%, Cdyn−20%, PEFR −25%, and $V_T$−15%. Patterson R, Harris, KE: Aerosolized Antigen Dose-response Studies in Asthmatic Monkeys. J. Lab. Clin. Med. 92:282-9 (1978).

Dilutions of Ascaris antigen and substance P (10 mg/ml) were prepared using sterile buffered saline. After an initial period of observation, a control solution of buffered saline was aerosolized. Patterson R, Harris KE: Aerosolized Antigen Dose-response Studies in Asthmatic Monkeys. J. Lab. Clin. Med. 92:282-9 (1978). Subsequently, substance P or buffered saline (for control challenges) was aerosolized and, after an additional 10 minutes, the monkey received an Ascaris antigen aerosol challenge.

Observations on Cutaneous Skin Titers

During the experiments described above, quantitative cutaneous endpoint testing was not a part of the prospective protocol because cutaneous titers were known to be relatively constant in the population of allergic monkeys. When the airway responses to Ascaris challenge in some animals suggested a change in the allergic status of the monkeys, quantitative endpoint cutaneous titrations were performed in all monkeys.

For each monkey studied, the results of cutaneous endpoint titer and airway response are recorded in Tables I and II showing changes in cutaneous endpoint titers to Ascaris antigen prior to and subsequent to administration of substance P and Ascaris antigen. A description of the experiment, results and interpretation are provided for each monkey.

Table III provides a summary of changes in endpoint titers to Ascaris antigen prior to and subsequent to administration of substance P and Ascaris antigen.

The statistical significance of the difference in the mean log of the cutaneous endpoint dilutions (pre versus post substance P and allergen) for all seven monkeys was assessed using the within-groups t-test. In the first analysis (Table IV, top), the log of the last cutaneous endpoint dilution preceding the substance P and allergen experiments was compared with the log of the first cutaneous endpoint dilution following substance P and allergen administration. The result suggested that there was a significant decrease in skin reactivity: $t(6) = -6.18$, $p = 0.001$. In the second analysis (Table IV, bottom), the mean log of all cutaneous endpoint dilutions preceding the substance P and allergen experiments was computed for each monkey as was the mean log of all cutaneous endpoint dilutions following substance P and allergen experiments. These means were also significantly different [$t(6) = -5.37$, $p = 0.002$], corroborating the finding of decreased skin reactivity following administration of substance P and allergen.

All monkeys that received aerosolized substance P and Ascaris antigen were found to have decreased skin reactivity. A graphic representation of the decline in cutaneous reactivity is shown for all monkeys in FIG. 2, 3, 5, 6, 7, and 8. This decrease in reactivity can be compared to FIG. 1 which shows the results of endpoint cutaneous titration to Ascaris in two untreated allergic monkeys that demonstrate the persistence of IgE antibody to Ascaris for many years. These results are typical of what has been observed in Ascaris skin reactive monkeys for over two decades of observation of this colony.

note that for periods of 3 to 12 years prior to substance P and Ascaris antigen, there is minimal change in the cutaneous endpoint titer (a one log change is within the limits of experimental error). In monkeys 95, 98, 90, 88, 97 and 448, there is a marked decline in the endpoint cutaneous titers after substance P and Ascaris antigen. Monkey 612 (FIG. 8) is the most erratic in endpoint cutaneous titers in the years prior to substance P and Ascaris antigen.

TABLE I

Monkey 448
History prior to treatment
with Substance P and Ascaris

| Year | Representative cutaneous endpoint titer | Total airway challenges | No. of positive airway responses |
|---|---|---|---|
| 1976-77 | $10^{-3}$ | 10 | 3 |

TABLE I-continued

| 1978-89 | $10^{-4}$ | 7 | 0 |
|---|---|---|---|

History subsequent to treatment with substance P and Ascaris

| Representative cutaneous end-point titer | Aerosol stimulus | Airway and response | | | |
|---|---|---|---|---|---|
| 1989 month | | | | | |
| 6 | | SP | Pos | A 1.5 | Pos |
| 6 | | S | Neg | A 1.5 | Neg |
| 7 | | SP | Neg | A 1.5 | Pos |
| 7 | | S | Neg | A 1.5 | Pos |
| 8 | | S | Neg | A 1.5 | Pos |
| 9 | | S | Neg | A 1.5 | Pos |
| 10 | | S | Neg | A 1.5 | Pos |
| 11 | | S | Neg | A 1.5 | Pos |
| 1990 month | | | | | |
| 6 | | S | Neg | A 1.5 | Neg |
| 7 | | SP | Neg | A 1.5 | Neg |
| 8 | $10^{-1}$ | SP | Neg | A 1.5 | Neg |
| 10 | Neg | ND | | | |
| 11 | $10^{-1}$ | ND | | | |
| 12 | Neg | ND | | | |
| 1991 month | | | | | |
| 2 | Neg | S | Neg | A 1.5 | Neg |
| 3 | Neg | ND | | | |

ND = not done, S = saline (control), SP = substance P, A = Ascaris antigen

Monkey 448
Description of the Experiment, the Results and Interpretation History: Prior to the experiment, monkey 448 was initially airway and skin reactive to Ascaris antigen (1976-77). Airway reactivity disappeared but cutaneous reactivity to Ascaris antigen persisted (1978-89).
Experiment: In 1989, monkey 448 received aerosolized substance P and Ascaris antigen. Airway responsiveness to Ascaris antigen occurred and persisted for several months even in the absence of aerosolized substance P. In 1990, monkey 448 had no response to substance P or Ascaris antigen alone or in combination. In late 1990 retesting of skin reactivity was done and the skin reactivity to Ascaris antigen became negative and has remained negative. See FIG. 7 for summary of cutaneous titers.
Interpretation: The aerosol experiments in 1989 show the enhanced airway reactivity to Ascaris antigen induced by substance P and Ascaris antigen. The disappearance of skin reactivity to Ascaris antigen later in 1989 is the first clue to the unexpected discovery that aerosolized substance P and Ascaris antigen terminates or decreases skin reactivity to an allergen.

Monkey 612
History prior to treatment with Substance P and Ascaris

| Years | Representative cutaneous end-point titer | Total airway challenges | No. of positive airway responses |
|---|---|---|---|
| 1977-79 | $10^{-3}$ | 16 | 14 |
| 1980 | | 6 | 5 |
| 1981 | | 4 | 2 |
| 1982-89 | $10^{-4}$ | 5 | 0 |

History subsequent to treatment with Substance P and Ascaris

| Representative cutaneous end-point titer | Aerosol stimulus | Airway and response | | | |
|---|---|---|---|---|---|
| 1989 month | | | | | |
| 6 | $10^{-3}$ | S | Neg | A 1.5 | Neg |
| 6 | | SP | Neg | A 1.5 | Pos |
| 7 | | SP | Neg | A 1.5 | Pos |
| 8 | | S | Neg | A 1.5 | Pos |
| 9 | | S | Neg | A 1.5 | Pos |
| 10 | | S | Neg | A 1.5 | Pos |
| 11 | | S | Neg | A 1.5 | Pos |
| 1990 month | | | | | |
| 1 | | S | Neg | A 1.5 | Neg |
| 6 | | S | Neg | A 1.5 | Neg |
| 7 | | S | Neg | A 1.5 | Neg |
| 7 | | SP | Neg | A 1.5 | Neg |
| 8 | $10^{-2}$ | SP | Neg | A 1.5 | Neg |
| 10 | $10^{-2}$ | ND | | | |
| 11 | $10^{-2}$ | ND | | | |
| 12 | $10^{-2}$ | ND | | | |
| 1991 month | | | | | |
| 2 | $10^{-2}$ | S | Neg | A 1.5 | Neg |
| 3 | $10^{-2}$ | ND | | | |

ND = not done, S = saline (control), SP = substance P, A = Ascaris antigen

Monkey 612
Description of the Experiment, the Results and Interpretation History: This monkey had a relatively consistent airway response to Ascaris antigen aerosol challenge in 1977-1979. This airway responsiveness decreased in 1980-1981 and was absent from 1982-1989, however, cutaneous reactivity persisted.
Experiment: This animal showed the effect of substance P and Ascaris antigen airway response because two substance P-Ascaris antigen exposures were followed by four responses to Ascaris antigen in the absence of substance P. This airway reactivity to Ascaris antigen was lost by January of 1990 and was not restored by substance P-Ascaris antigen aerosol exposures in July and August 1990.
The cutaneous titer to Ascaris antigen was $10^{-3}$ in June of 1989 and decreased to $10^{-2}$ in 1990 and remained at $10^{-2}$ in 1991. See FIG. 8 for summary of cutaneous titers.
Interpretation: This monkey had the least reduction of cutaneous titer of any of the seven monkeys and the one log reduction is within the limits of experimental error so no reduction may have occurred. Alternatively we suspect that there may have been a transient increase in cutaneous titer in July of 1989 and then a more significant decline. This hypothesis will have to be proven or disproven in future experiments.

Monkey 98
History prior to treatment with Substance P and Ascaris

| Year | Representative endpoint cutaneous titer | Airway Challenge with A, dilution and response | | | |
|---|---|---|---|---|---|
| 1985 | $10^{-11}$ | S | Neg | A 1:5 | Neg |
| 1985 | | S | Neg | A 1:5 | Pos |
| 1986 | $10^{-11}$ | S | Neg | A 1:5 | Pos |
| 1986 | | S | Neg | A 1:5 | Neg |
| 1986 | | S | Neg | A 1:5 | Neg |

History subsequent to treatment with Substance P and Ascaris

| Month | Year | | | | | |
|---|---|---|---|---|---|---|
| 5 | 1989 | $10^{-10}$ | S | Neg | A 1:25 | Neg |
| 6 | 1989 | | SP | Neg | A 1:25 | Neg |
| 8 | 1989 | | S | Neg | A 1:25 | Neg |
| 9 | 1989 | | SP | Neg | A 1:25 | Pos |
| 10 | 1989 | | S | Neg | A 1:25 | Pos |
| 7 | 1990 | | S | Neg | A 1:25 | Neg |
| 7 | 1990 | | SP | Neg | A 1:25 | Pos |
| 8 | 1990 | $10^{-4}$ | S | Neg | A 1:25 | Pos |
| 10 | 1990 | $10^{-4}$ | ND | | | |
| 11 | 1990 | $10^{-4}$ | ND | | | |
| 12 | 1990 | $10^{-4}$ | ND | | | |
| 2 | 1991 | $10^{-4}$ | S | Neg | A 1:5 | Pos |
| 3 | 1991 | $10^{-4}$ | ND | | | |

ND = not done, S = saline (control), SP = substance P, A = Ascaris antigen

Monkey 98
Description of the Experiment, the Results and Interpretation History: This monkey had marked cutaneous reactivity at an endpoint dilution titer of $10^{-11}$ in 1985 and 1986 but only two airway challenges of five with Ascaris antigen which were positive. Therefore, the monkey was not challenged with Ascaris antigen again by aerosol.
Experiments: The monkey entered the substance

TABLE I-continued

P-Ascaris antigen aerosol study and was skin test positive to Ascaris antigen at $10^{-10}$, a one log decrease from 1986. Substance P and Ascaris antigen aerosol converted the monkey to a positive airway response at a 1:25 dilution of Ascaris antigen in September of 1989 and this responsiveness to the 1:25 dilution of Ascaris antigen persisted through August of 1990. However, the cutaneous titer dropped to $10^{-4}$ in August of 1990 and has remained at that level. Airway response is positive but only at 1:5 Ascaris antigen. See FIG. 3 for summary of cutaneous titers.
Interpretation: Positive airway responsiveness occurred after substance P-Ascaris antigen but the cutaneous titer declined six logs over 13 months when previously this titer had remained relatively constant for three years without Ascaris antigen skin testing or Ascaris antigen aerosol exposure.

Monkey 95
History prior to treatment with Substance P and Ascaris

| Years | Representative endpoint cutaneous titer | Airway challenge with A, diluton and response | | | |
|---|---|---|---|---|---|
| 1985 to 1988 | $10^{-8}$ | S | Neg | A | Pos at 1:5 or 1:10 |

History subsequent to treatment with Substance P and Ascaris

| Month | Year | | | | Airway challenge with A, dilution and response | | |
|---|---|---|---|---|---|---|---|
| 5 | 1988 | | SP | Neg | A | 1:5 | Pos |
| 5 | 1989 | $10^{-9}$ | S | Neg | A | 1:25 | Neg |
| 6 | 1989 | | SP | Neg | A | 1:25 | Pos |
| 8 | 1989 | | S | Neg | A | 1:25 | Pos |
| 9 | 1989 | | SP | Neg | A | 1:25 | Pos |
| 10 | 1989 | | S | Neg | A | 1:25 | Pos |
| 7 | 1990 | | S | Neg | A | 1:25 | Neg |
| 8 | 1990 | | SP | Neg | A | 1:25 | Pos |
| 8 | 1990 | $10^{-3}$ | S | Neg | A | 1:25 | Pos |
| 9 | 1990 | $10^{-3}$ | ND | | | | |
| 10 | 1990 | $10^{-3}$ | ND | | | | |
| 11 | 1990 | $10^{-4}$ | ND | | | | |
| 12 | 1990 | $10^{-4}$ | ND | | | | |
| 2 | 1991 | $10^{-4}$ | S | Neg | A | 1:5 | Pos |
| 3 | 1991 | $10^{-4}$ | ND | | | | |

ND = not done, S = saline (control), SP = substance P, A = Ascaris antigen

Monkey 95
Description of the Experiment, the Results and Interpretation

History: Monkey 95 had a skin test titer of $10^{-8}$ in 1985 and 1986. The monkey did not have an airway response to dilutions of Ascaris antigen higher than 1:5 or 1:10 so this monkey was entered into the substance P-Ascaris antigen experiment.
Experiment: At onset in May of 1989, Monkey 95 had a skin test titer of $10^{-9}$ and was negative to Ascaris antigen airway challenge at a 1:25 dilution of Ascaris antigen, substance P-Ascaris antigen aerosol exposures converted the animal to a positive Ascaris antigen response at 1:25 dilution of Ascaris antigen which remained positive at 1:25 for several months but is only positive at 1:5 in 1991. The cutaneous titer declined from $10^{-9}$ to $10^{-3}$ and now remains consistently positive at $10^{-4}$. See FIG. 2 for summary of cutaneous titers.
Interpretation: The airway response increased after substance P-Ascaris antigen but then decreased. The cutaneous titer decreased initially six logs and has remained constant with a five log decrease from May of 1989 when it was $10^{-9}$.

Monkey 97
History prior to treatment with Substance P and Ascaris

| Years | Representative cutaneous end-point titer | Total # airway challenges | No. of positive airway responses |
|---|---|---|---|
| 1985-87 | $10^{-11}$ | 3 | 0 |

History subsequent to treatment with Substance P and Ascaris

| Month | Year | | | Airway challenge with A, diluton and response | | |
|---|---|---|---|---|---|---|
| 11 | 1987 | $10^{-8}$ | | | | |
| 12 | 1987 | | SP | Pos | A | *see below |
| 2 | 1988 | | SP | Neg | A | *see below |
| 5 | 1988 | $10^{-8}$ | SP | Neg | A | *see below |
| 5 | 1989 | | S | Neg | A | Neg |
| 6 | 1989 | | SP | Neg | A | *see below |
| 10 | 1989 | | S | Neg | A | Neg |
| 7 | 1990 | | SP | Neg | A | *see below |
| 8 | 1990 | $10^{-1}$ | SP | Neg | A | Neg |
| 10 | 1990 | $10^{-2}$ | ND | | | |
| 11 | 1990 | $10^{-3}$ | ND | | | |
| 12 | 1990 | $10^{-3}$ | ND | | | |
| 2 | 1991 | $10^{-3}$ | S | Neg | A | Neg |
| 3 | 1991 | $10^{-3}$ | ND | | | |

ND = not done, S = saline (control), SP = substance P, A = Ascaris antigen
*two Pulmonary function parameters positive - Pulmonary resistance and Dynamic compliance

Monkey 97
Description of the Experiment, the Results and Interpretation

History: This monkey had an endpoint cutaneous titer of $10^{-11}$ in 1985 and was consistently negative to airway challenge with Ascaris antigen (three challenges).
Experiment: Monkey 97 was entered into the study of substance P and Ascaris antigen aerosol challenge in 1987 at which time the cutaneous titer was $10^{-8}$ and remained $10^{-8}$ in 1988. We observed that substance P and Ascaris antigen did not result in a complete asthmatic airway response but did result in positive airway responses in two pulmonary function parameters. These were pulmonary resistance and dynamic compliance (abbreviated $R_L$ and Cdyn). These two abnormalities in pulmonary function were positive in five experiments and then became negative. After the substance P and Ascaris antigen aerosol challenges the cutaneous titer to Ascaris antigen dropped to $10^{-1}$ and then increased and has remained constant at $10^{-3}$. See FIG. 6 for summary of cutaneous titers.
Interpretation: Substance P-Ascaris antigen challenge altered the airway response in two pulmonary function parameters probably representing large airway obstruction. The substance P-Ascaris antigen aerosol exposures were intense (6) in this experiment and were followed by a seven log decrease in cutaneous titers followed by an increase in two logs and then a constant titer.

Monkey 90
History prior to treatment with Substance P and Ascaris

| Years | Representative cutaneous end-point titer | Total # airway challenges | No. of positive airway responses |
|---|---|---|---|
| 1985 | $10^{-6}$ | 2 | 2 |
| 1986 | $10^{-9}$ | 7 | 0 |

History subsequent to treatment with Substance P and Ascaris

| | Representative cutaneous end-point titer | Aerosol stimulus | | Airway and response | | |
|---|---|---|---|---|---|---|
| 1987 month | | | | | | |
| 11 | | SP | Neg | A | 1:50 | Pos |
| 12 | | S | Neg | A | 1:50 | Pos |
| 1988 month | | | | | | |
| 2 | | SP | Pos | A | 1:50 | Pos |
| 9 | $10^{-11}$ | | | | | |
| 1989 month | | | | | | |
| 5 | | S | Neg | A | 1:100 | Pos |
| 1990 month | | | | | | |
| 8 | $10^{-5}$ | ND | | | | |

TABLE I-continued

| | | | | | | |
|---|---|---|---|---|---|---|
| 10 | $10^{-4}$ | ND | | | | |
| 11 | $10^{-4}$ | ND | | | | |
| 12 | $10^{-4}$ | ND | | | | |
| 1991 month | | | | | | |
| 2 | $10^{-4}$ | S | Neg | A | 1:5 | Pos |
| 3 | $10^{-4}$ | ND | | | | |

ND = not done, S = saline (control), SP = substance P, A = Ascaris antigen

Monkey 90
Description of the Experiment, the Results and Interpretation

Figure 4:
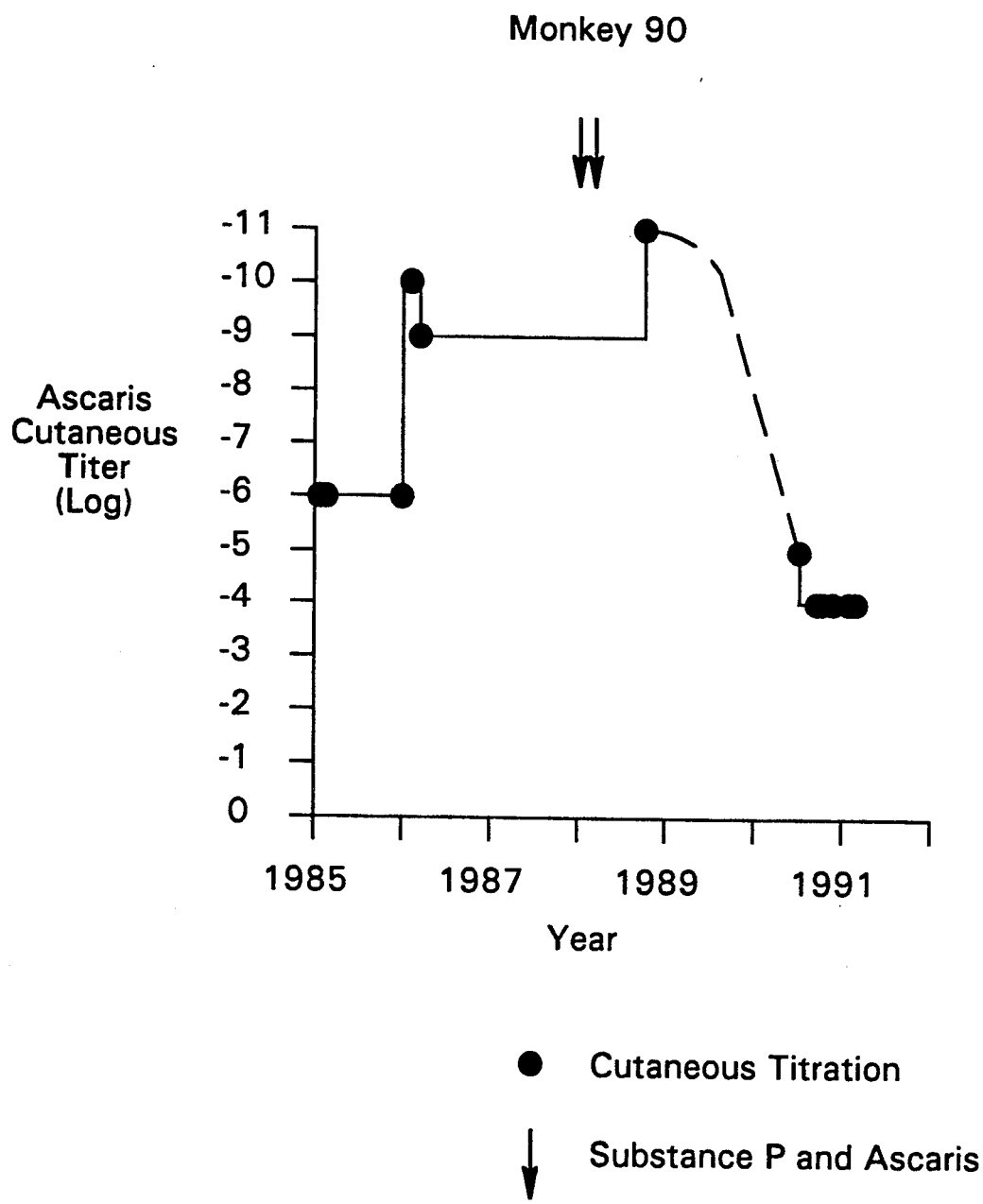
FIG. 4 shows Ascaris endpoint cutaneous titers of monkey 90.
Figure 5:
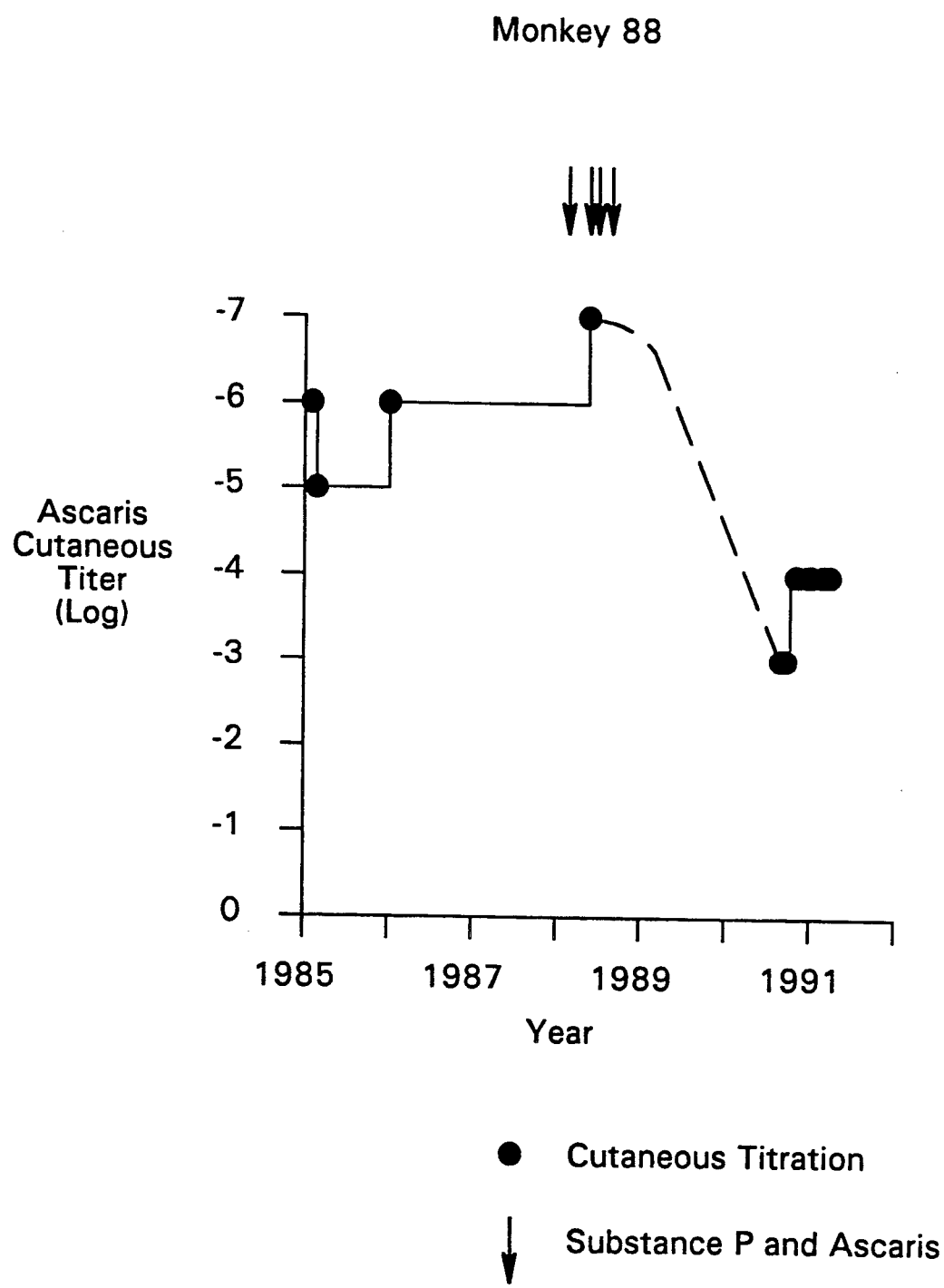
FIG. 5 shows Ascaris endpoint cutaneous titers of monkey 88.
Figure 6:
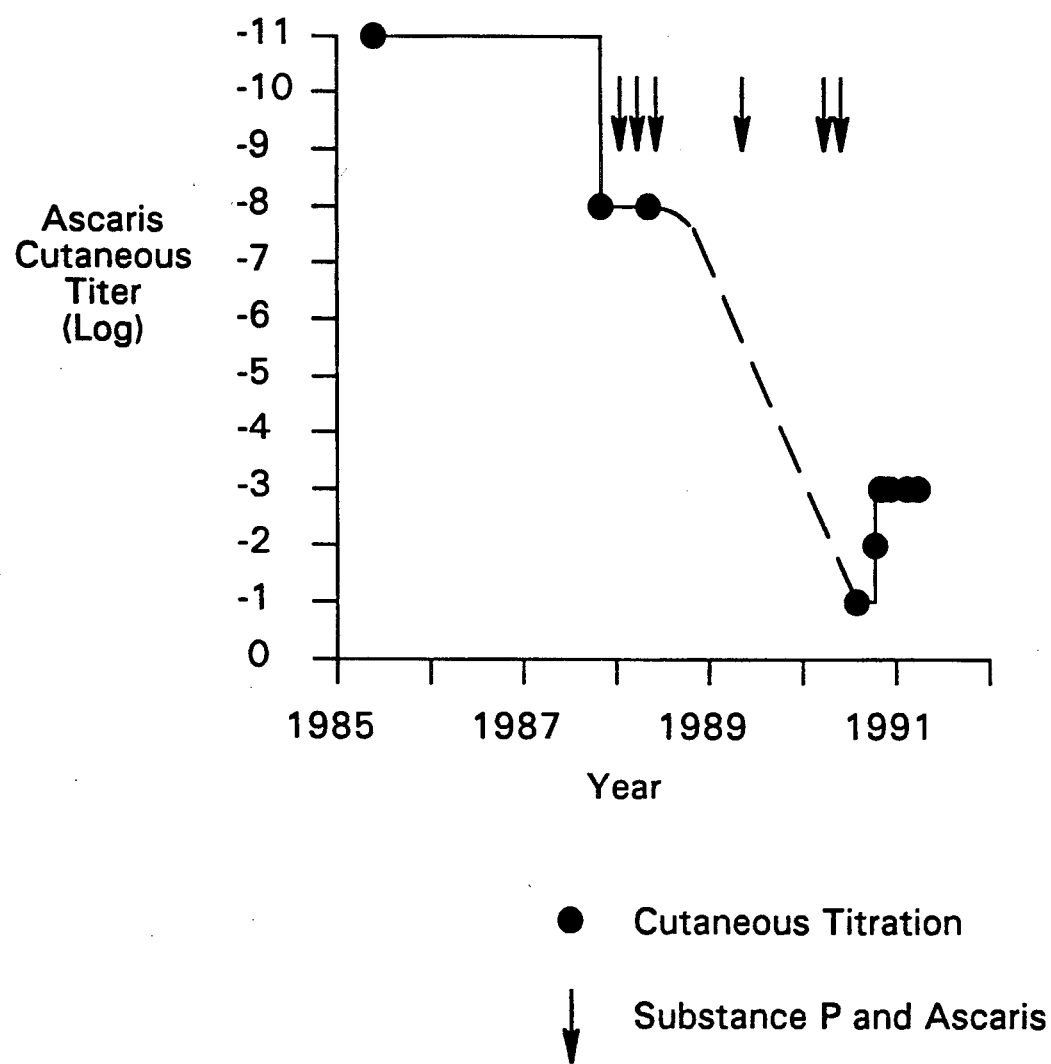
FIG. 6 shows Ascaris endpoint cutaneous titers of monkey 97.
Figure 7:
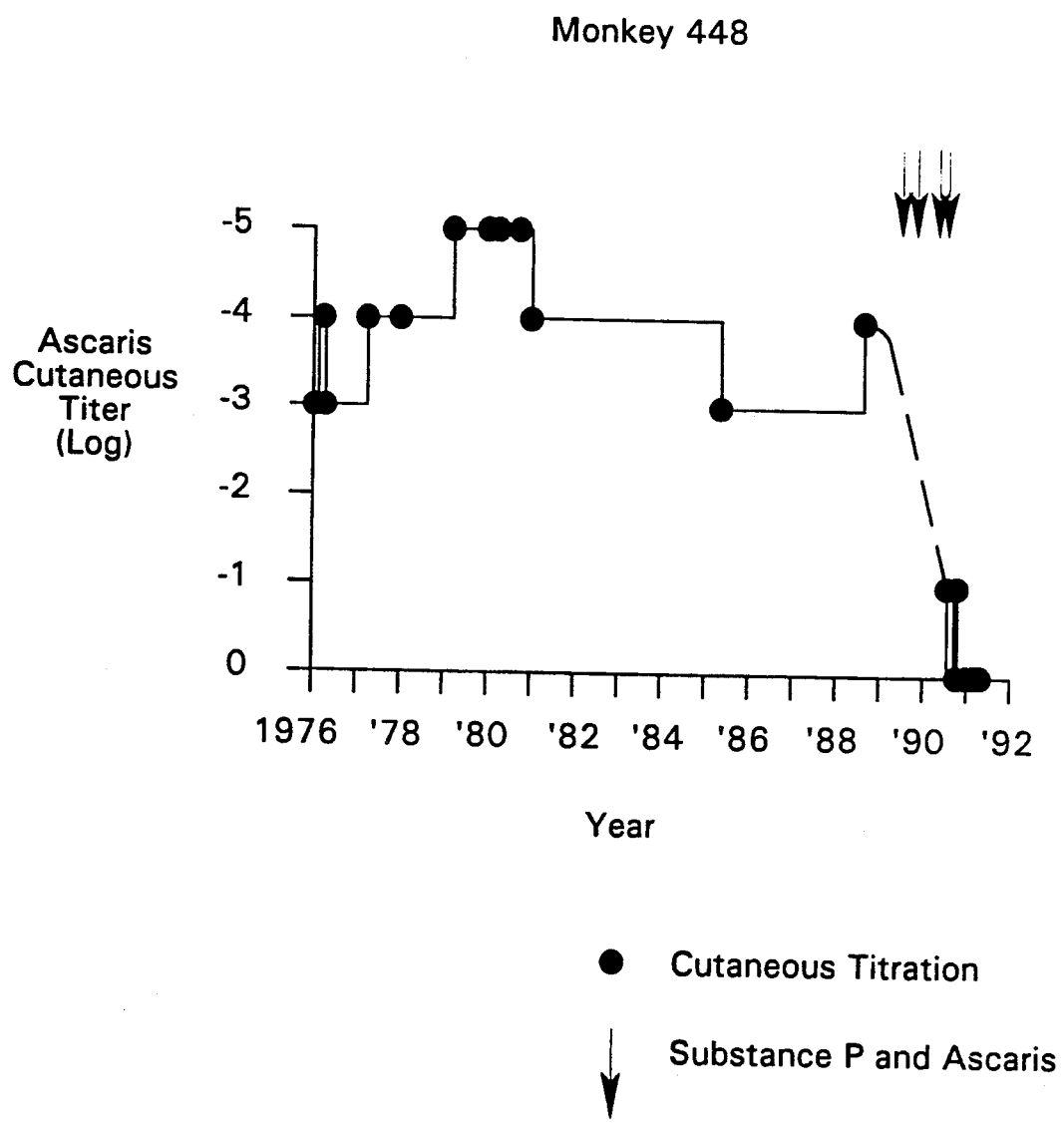
FIG. 7 shows Ascaris endpoint cutaneous titers of monkey 448.
Figure 8:
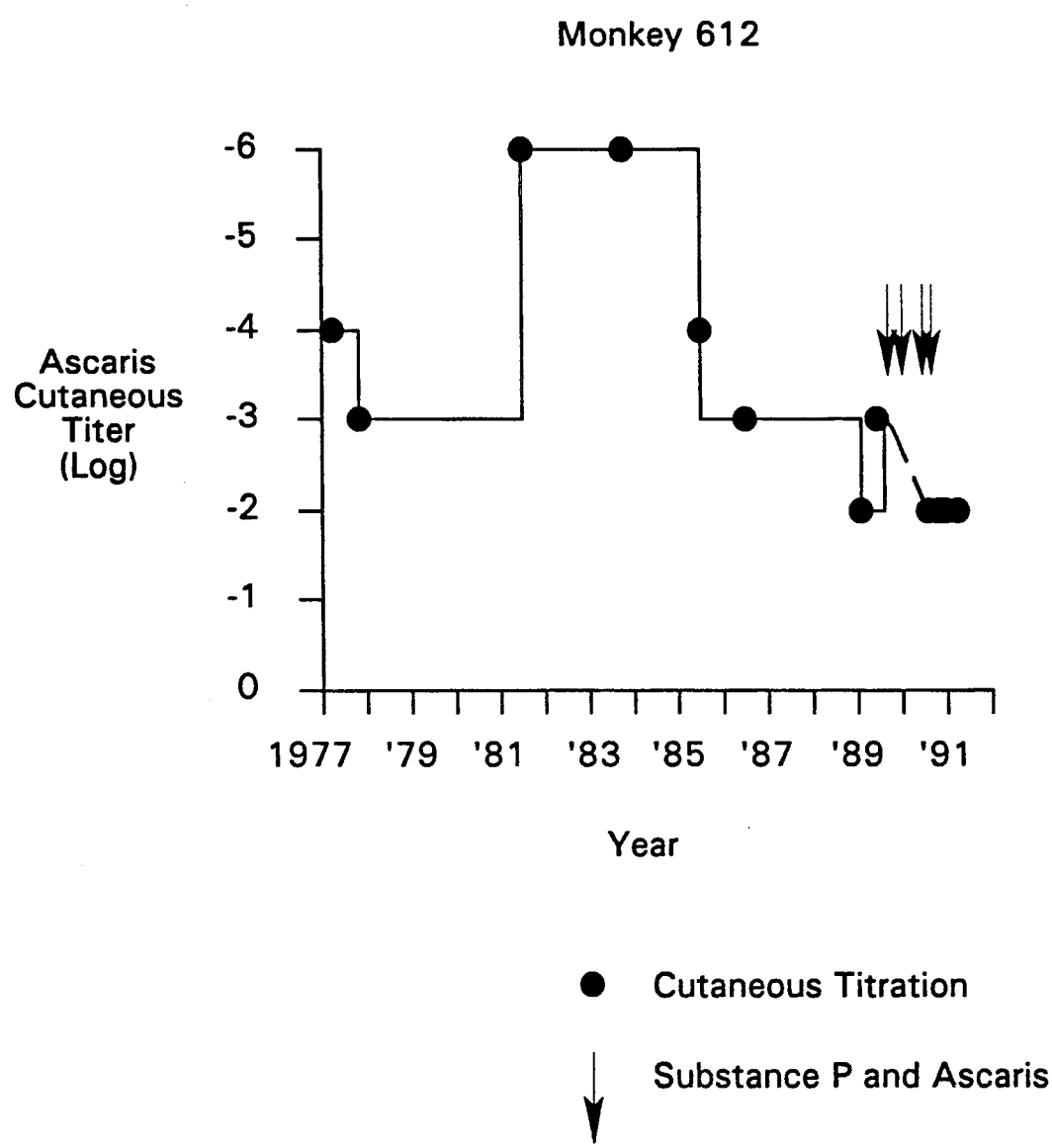
FIG. 8 shows Ascaris endpoint cutaneous titers of monkey 612.

History: This monkey had cutaneous reactivity of $10^{-6}$ to $10^{-10}$ from 1985 to 1986. This monkey was reactive to Ascaris antigen aerosol during 1985. Experiment: This monkey was used in pilot studies with substance P and Ascaris antigen aerosol challenge at a time when we were looking at preliminary experiments to define a protocol for studying the effect of the neurokinin substance P and Ascaris antigen on the asthmatic response, after substance P and a 1:50 concentration of Ascaris antigen in 1987, the next exposure of substance P + Ascaris antigen was in February 1988 and an increased titer of $10^{-11}$ was noted in September of 1988. The monkey was not skin tested again until August of 1990 and October of 1990 when the titers were $10^{-5}$ and $10^{-4}$, respectively. See FIG. 4 for summary of cutaneous titers.

Interpretation: In evaluating the experiment and the results, it must be remembered that this was a pilot experiment, not a defined protocol and the experiments were not designed to evaluate skin titers. The rise of titer to $10^{-11}$ in September of 1988 may have been the result of Ascaris antigen exposure on February of 1988 with an anamnestic response. The subsequent decline to $10^{-5}$ may have occurred much earlier than August of 1990 and may thus have been due to the substance P + Ascaris antigen exposure in September of 1988.

EXAMPLE 2

Monkey 88 was tested as previously described in example 1 except it twice received an aerosol challenge with Ascaris antigen and then substance P at 10 minutes post Ascaris antigen challenge, and once received substance P and then 10 minutes post substance P received a challenge with Ascaris antigen.

TABLE II

Monkey 88

History prior to treatment with Substance P and Ascaris

| Years | Representative cutaneous end-point titer | Total # airway challenges | No. of positive airway responses |
|---|---|---|---|
| 1985-86 | $10^{-6}$ | 7 | 7 |

History subsequent to treatment with Substance P and Ascaris

| | Representative cutaneous end-point titer | Aerosol stimulus | and | Airway response | | |
|---|---|---|---|---|---|---|
| 1988 month | | | | | | |
| 1 | | A | Pos | SP | | Pos |
| 5 | $10^{-7}$ | SP | Pos | A | | Neg |
| 5 | | A | Pos | SP | | Pos |
| 6 | | SP | Pos | A | | Pos |
| 1990 month | | | | | | |
| 9 | $10^{-3}$ | ND | | | | |
| 10 | $10^{-3}$ | ND | | | | |
| 11 | $10^{-4}$ | ND | | | | |
| 12 | $10^{-4}$ | ND | | | | |
| 1991 month | | | | | | |
| 2 | $10^{-4}$ | S | Neg | A | 1:5 | Pos |

TABLE II-continued

Monkey 88

| | | |
|---|---|---|
| 3 | $10^{-4}$ | ND |

ND = not done, S = saline (control), SP = substance P, A = Ascaris antigen

Description of the Experiment, the Results and Interpretation

History: This monkey had a cutaneous titer of $10^{-5}$ to $10^{-6}$ in 1985 and 1986 and $10^{-7}$ in 1988.

Experiment: The monkey was studied in a series of experiments during which it received aerosol exposure to Ascaris antigen and substance P or substance P and Ascaris antigen. Positive airway responses occurred with either sequence. The cutaneous titer subsequently dropped to $10^{-3}$ in 1990 and has increased to $10^{-4}$ where it remains. See FIG. 5 for summary of cutaneous titers.

Interpretation: Airway response to Ascaris antigen or substance P occur after either sequence of administration of these agents by aerosol. After five experiments the cutaneous titer declined four logs and then remained constant with a three log decrease. This monkey will not be reported in our research publication because the protocol varies from the substance P-Ascaris antigen sequence subsequently used.

TABLE III

| Monkey No. | Yrs. Studied | Variations in skin titers from last test prior to SP (logs) | After SP* (logs) | Variation in logs after SP as of 3/21/91 |
|---|---|---|---|---|
| | | ↑ | ↓ | |
| 448 | 14 | 4 | 4 | 4 | 4 |
| 612 | 13 | 4 | 5 | 1 | 1 |
| 97 | 5 | 0 | 3 | 8 | 5 |
| 98 | 5 | 1 | 0 | 8 | 8 |
| 88 | 5 | 1 | 2 | 4 | 3 |
| 90 | 5 | 4 | 1 | 6 | 7 |
| 95 | 5 | 0 | 0 | 6 | 5 |
| TOTALS | 52 yrs. studied | 14 logs ↑ | 15 logs ↓ | 37 logs ↓ | 33 final logs** ↓ |

*Cutaneous titers done in August-September 1990
**Total of 10 years studied

Summary of changes in endpoint titers to Ascaris antigen prior to and subsequent to administration of substance P and Ascaris antigen.

Columns 3 and 4 show the variations in skin titers over the years each monkey was studied (shown in column 2). These titers increased 14 logs in a total of 52 years the monkeys were studied and decreased 15 logs. Thus the cumulative variation was one log over these years prior to exposure to substance P and Ascaris by aerosol.

After exposure to substance P plus Ascaris, the cutaneous titers declined in all monkeys for a total of 37 logs decrease over 10 years of total observation. Minimal changes occurred over the 7 months for a final decrease of 33 logs.

The results of the foregoing examples showing a decrease in IgE mediated cutaneous reactivity in rhesus monkeys were the result of a serendipitous observation while we were studying the effects of substance P and allergen on rhesus airways. The results of decline of IgE antibody occurred after aerosol administration of substance P followed by allergen in the same experiment. We, therefore, conclude from the data that the neurokinin, substance P, and allergen down regulated the production of IgE antibody in the pulmonary immunologic compartment, systemically or both. The mechanism involved is not yet known with certainty. Such a change may have resulted from direct action on B lymphocytes producing specific IgE, or by inhibiting B cell production of IgE as a result of stimulating inhibitory T cells.

TABLE IV

Results of Statistical Analysis Using Within Groups T-Test Comparing The Logs of Cutaneous Endpoint Dilutions Pre and Post substance P (SP) and Ascaris (A).

| Monkey Number | Log of Last Cutaneous Endpoint Before SP and A Administration | Log of First Cutaneous Endpoint After SP and A Administration |
|---|---|---|
| 88 | −6 | −3 |
| 90 | −9 | −5 |
| 95 | −8 | −3 |
| 97 | −8 | −2 |
| 98 | −10 | −4 |
| 448 | −4 | 0 |
| 612 | −3 | −2 |
| All monkeys: | | |

TABLE IV-continued

Results of Statistical Analysis Using Within Groups T-Test Comparing The Logs of Cutaneous Endpoint Dilutions Pre and Post substance P (SP) and Ascaris (A).

| Mean ± S.D. | −6.9 ± 1.8 | −2.7 ± 1.6 |
|---|---|---|
| | | t value −6.18 |
| | | p value 0.001 |
| Monkey Number | Means of the Logs of Cutaneous Endpoint Titers of Individual Monkeys Pre SP and A | Means of the Logs of Cutaneous Endpoint Titers of Individual Monkeys Post SP and A |
| 88 | −6.0 | −3.7 |
| 90 | −7.4 | −4.2 |
| 95 | −8.4 | −3.6 |
| 97 | −9.5 | −2.5 |
| 98 | −11 | −4.0 |
| 448 | −4.1 | −0.3 |
| 612 | −3.8 | −2.0 |
| Mean of the Log of Cutaneous Endpoint Titers of All monkeys | | |
| Mean ± S.D. | −7.2 ± 2.7 | −2.9 ± 1.4 |
| | | t value −5.37 |
| | | p value 0.002 |

S.D. = standard deviation

EXAMPLE 3

Cutaneous titer to rye grass antigen in a human subject is shown in the following example. A patient received 1:10,000 dilution administration of rye grass allergen. This dilution had been the patient's endpoint prior to immediately after the substance P and allergen administration by the aerosol protocol of Table V.

TABLE V

Sequence of Substance P(SP) Rye Grass Aerosol Administration in a Human Subject

| Date Administered | Compound Administered |
|---|---|
| 03/25/91 | 10 to 1000 AU/ml Rye Grass |
| 04/08/91 | SP-2mg plus 10 to 1000 AU/ml Rye Grass |
| 04/15/91 | SP-4mg plus 10 to 1000 AU/ml Rye Grass |
| 04/22/91 | SP-4mg plus 10 to 1000 AU/ml Rye Grass |

TABLE V-continued

Sequence of Substance P(SP) Rye Grass Aerosol Administration in a Human Subject

| Date Administered | Compound Administered |
|---|---|
| 05/07/91 | SP-4mg plus 10 to 1000 AU/ml Rye Grass |

Following the aerosol protocol, the patient was further evaluated by intracutaneous injections of rye grass allergen at the above-stated 1:10,000 dilution.

Figure 9A:
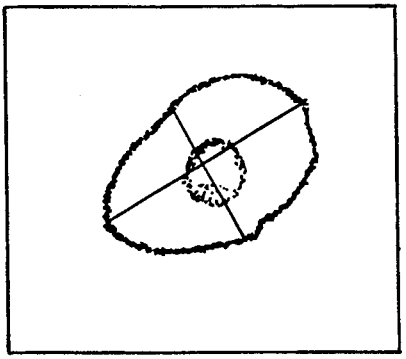
FIG. 9A, 9B, 9C, 9E and 9E show, sequentially grass in a human subject as a wheal/flare reaction.
Figure 9B:
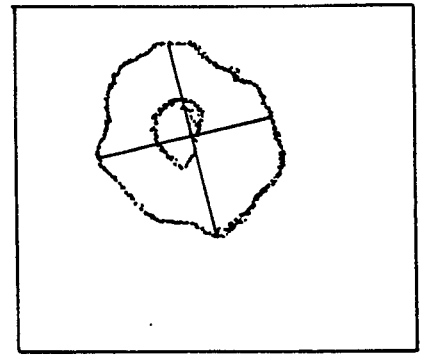
Figure 9C:
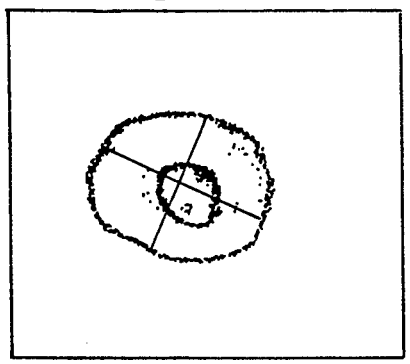
Figure 9D:
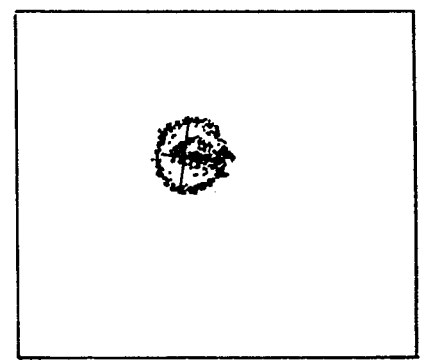
Figure 9E:
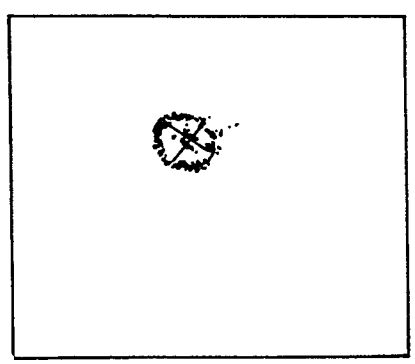
Figure 10:
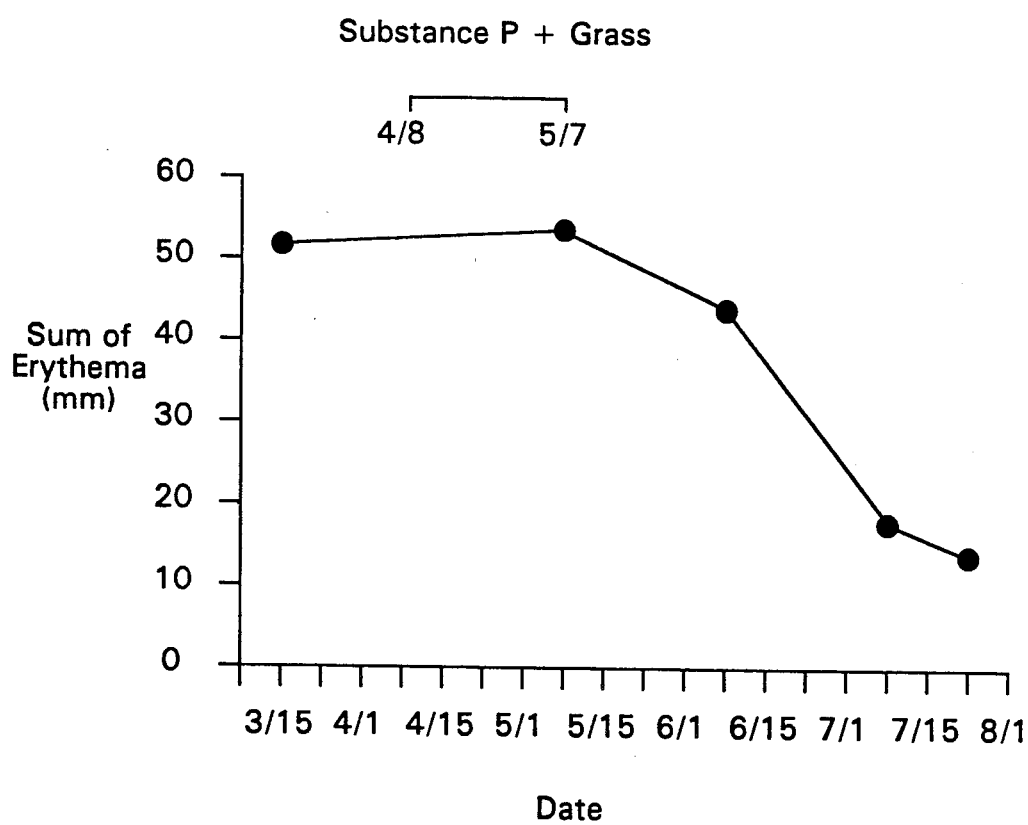
FIG. 10 shows sum of erythema measurement versus dates in 1991 for human subject receiving substance P and rye grass antigen.
Figure 11:
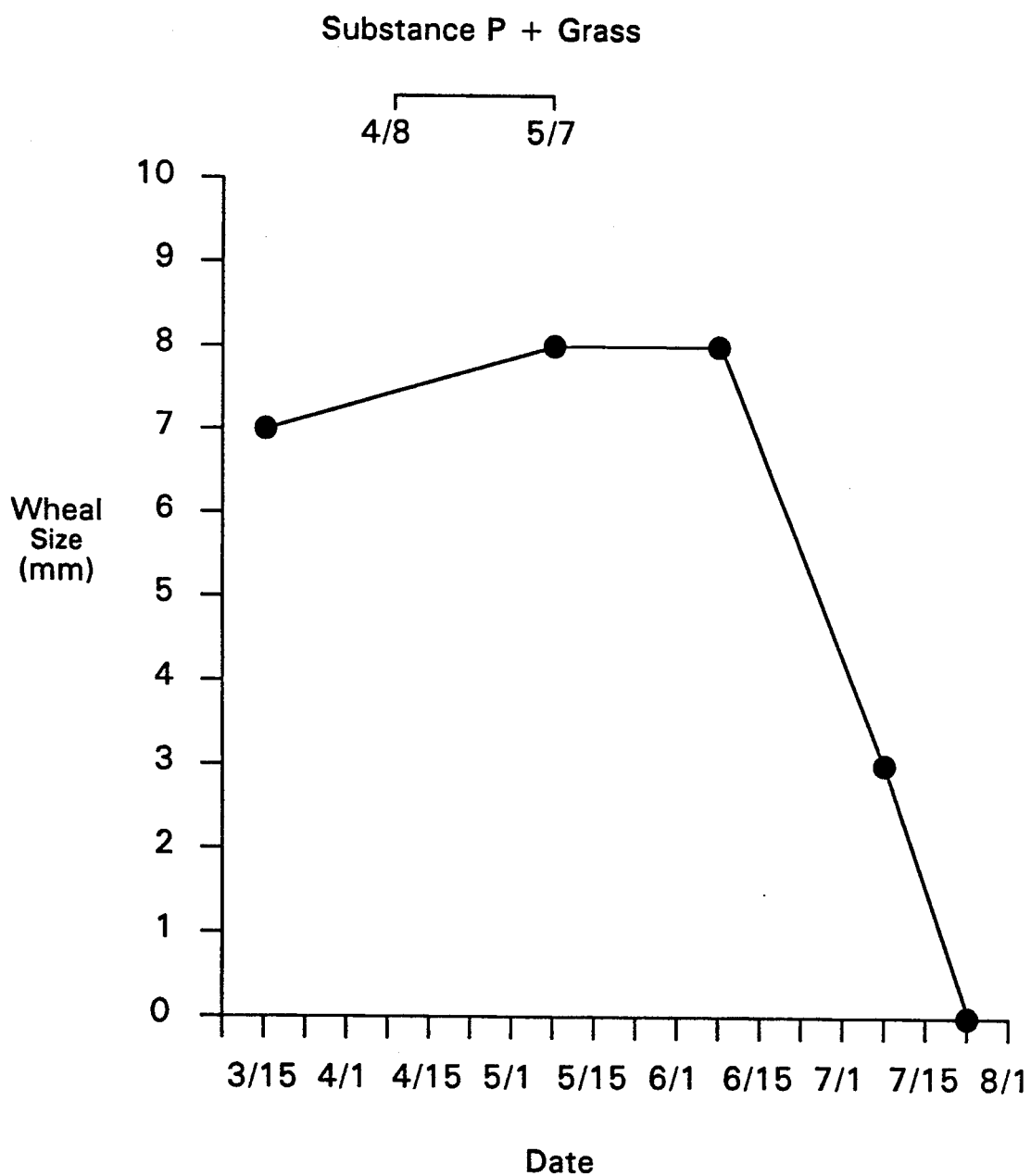
FIG. 11 shows wheal size in mm versus dates in 1991 for human patient receiving substance P and rye grass antigen.

In monitoring the change in cutaneous reactivity, using standard methodology, two parameters were followed the size of the wheal (the bump which occurs in the central area where the skin test is injected) and the size of the erythema (the area of redness around the wheal). For a permanent record, the areas of wheal and erythema are traced with a pen and then a piece of tape is applied over the tracing and removed. An imprint is left on the tape. The tape is then applied to a piece of paper and this provides a permanent record. FIGS. 9A, 9B, 9C, 9D and 9E are copies of the tracings of the subject's cutaneous responses at 1:10,000 at various times. FIG. 9A is the baseline of Mar. 15, 1991 which was used as a basis for measurements to determine the extent of erythema. FIGS. 9B, 9C, 9D and 9E are the subject's cutaneous responses, respectively, on May,10, and June 12, July 12, and Jul. 22, 1991. FIG. 10, shows, the decrease in the sum of erythema and FIG. 11, shows the decrease in the size of the wheal.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method of treating a mammal having an IgE mediated allergy to a specific allergen, comprising administering said allergen to said mammal by a non-oral route which results in systemic absorption of the allergen, and concurrently therewith also administering substance P to said mammal by a non-oral route which results in systemic absorption of substance P, said allergen and said substance P being administered in amounts effective to reduce the mammal's skin allergic reaction to the allergen.

2. The method of claim 1 in which said concurrent administrations are periodically repeated to further reduce the mammal's allergic reaction.

3. The method of claim 1 or 2 in which said mammal is selected from humans, dogs, cats and horses.

4. The method of claims 1 or 2 in which said mammal is a human.

5. The method of claims 1 or 2 in which said mammal is a dog.

6. The method of claims 1 or 2 in which said mammal is a cat.

7. The method of claims 1 or 2 in which said mammal is a horse.

8. The method of treating a human having an IgE mediated allergy to a specific allergen, comprising administering said allergen and substance P by a parenteral route which results in their systemic absorption, said allergen and said substance P being administered in amounts effective to reduce the human's skin allergic reaction to the allergen.

9. The method of claim 8 in which said allergen and substance P are administered by simultaneous subcutaneous injection.

10. The method of claim 8 or 9 in which said administration is periodically repeated to further reduce said skin allergic reaction.

* * * * *

UNITED STATES PATENT AND TRADEMARK OFFICE
CERTIFICATE OF CORRECTION

PATENT NO. : 5,314,690
DATED : May 24, 1994
INVENTOR(S) : Patterson and Harris

Figure 1A:
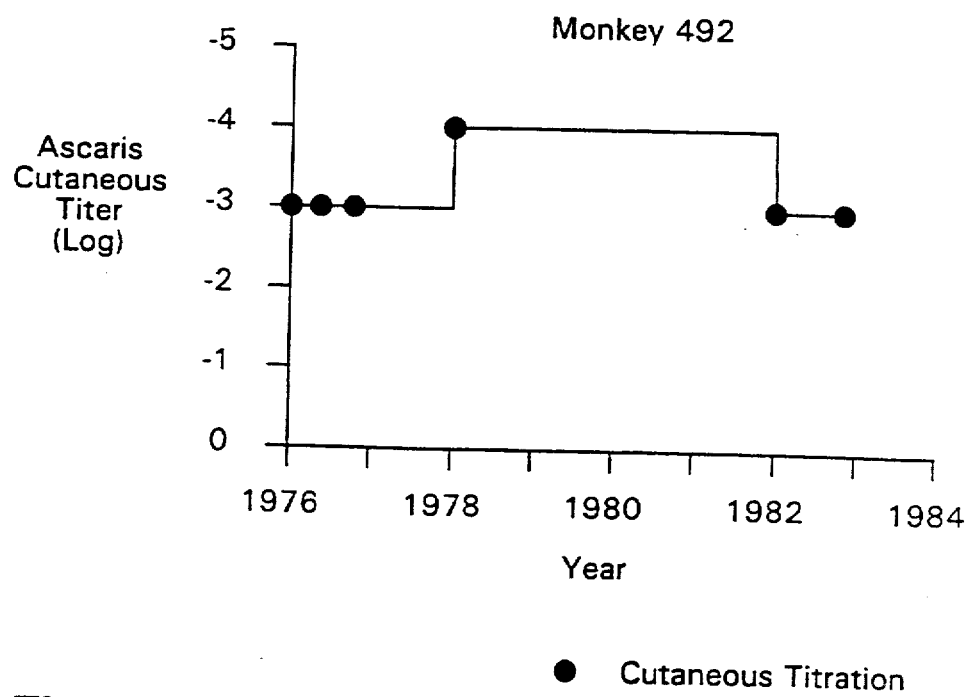
FIGS. 1A and 1B show the Ascaris endpoint cutaneous titer of IgE that is typical in monkeys allergic to Ascaris antigen showing persistence of IgE antibody for a period of several years.
Figure 1B:
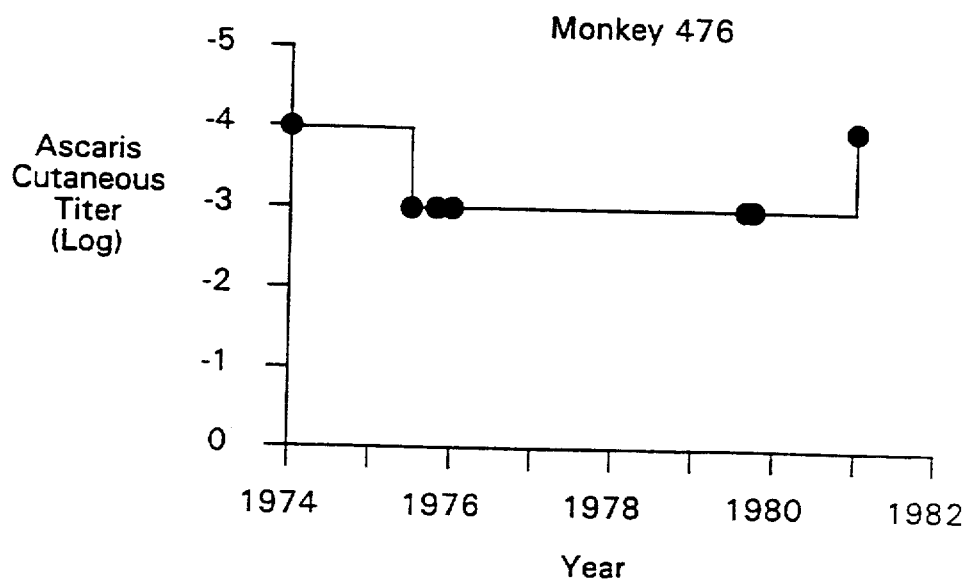

It is certified that error appears in the above-indentified patent and that said Letters Patent is hereby corrected as shown below:

In the Drawings, before Figure 2, insert attached copy of Figure 1A and 1B.

In claim 8, column 20, line 54, delete "The method" and insert -- A method --.

Signed and Sealed this

Twenty-third Day of August, 1994

Attest:

Attesting Officer

BRUCE LEHMAN
Commissioner of Patents and Trademarks

● Cutaneous Titration

UNITED STATES PATENT AND TRADEMARK OFFICE
CERTIFICATE OF CORRECTION

PATENT NO. : 5,314,690
DATED : May 24, 1994
INVENTOR(S) : Patterson and Harris

It is certified that error appears in the above-indentified patent and that said Letters Patent is hereby corrected as shown below:

In Column 10, line 43, after "3," insert -- 4, --.

In Column 11, delete "1.5" and insert -- 1:5 --.

In Column 12, delete "1.5" and insert -- 1:5 --.

In Column 17, line 28, after "to" insert -- and --.

Signed and Sealed this

Twelfth Day of September, 1995

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

Arg  Pro  Lys  Pro  Gln  Gln  Phe  Phe  Gly  Leu  Met
    1                 5                        10

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown (ii) MOLECULE TYPE: peptide (xi) SEQUENCE DESCRIPTION: SEQ ID NO:2:

Phe Phe Gly Leu Met
1               5

(2) INFORMATION FOR SEQ ID NO:3:

(i) SEQUENCE CHARACTERISTICS:
    (A) LENGTH: 6 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:3:

Glu Phe Phe Gly Leu Met
1                   5

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:4:

Arg Pro Lys Pro
1

(2) INFORMATION FOR SEQ ID NO:5:

(i) SEQUENCE CHARACTERISTICS:
    (A) LENGTH: 4 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:5:

Gly Pro Arg Pro
1